United States Patent [19]
Reitz et al.

[11] Patent Number: 5,922,731
[45] Date of Patent: *Jul. 13, 1999

[54] 5-[(HETEROARYL)ALKYL]-3-OXO-PYRIDO [1,2-A]BENZIMIDAZOLE-4-CARBOXAMIDE DERIVATIVES USEFUL IN TREATING CENTRAL NERVOUS SYSTEM DISORDERS

[75] Inventors: Allen B. Reitz, Lansdale; Louis J. Fitzpatrick, Souderton; Alfonzo D. Jordan, Horsham; Pauline J. Sanfilippo, Chester Springs, all of Pa.

[73] Assignee: Ortho Pharmaceutical Corporation, Raritan, N.J.

[ * ] Notice: This patent is subject to a terminal disclaimer.

[21] Appl. No.: 08/884,804

[22] Filed: Jun. 30, 1997

[51] Int. Cl.$^6$ .................. A61K 31/44; C07D 471/00; C07D 498/00; C07D 513/00
[52] U.S. Cl. ............................. 514/292; 546/86
[58] Field of Search ................. 546/86; 514/292

[56] References Cited

U.S. PATENT DOCUMENTS 5,639,760  6/1997  Maryanoff et al. .................... 514/292

*Primary Examiner*—Richard L. Raymond
*Assistant Examiner*—Bruck Kifle

[57] ABSTRACT

A compound of the general formula 1;

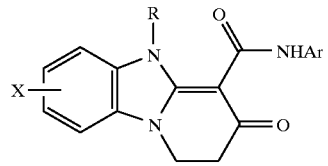

(1).

is disclosed as useful in treating disorders of the central nervous system. Pharmaceutical compositions and methods of treatment are also disclosed.

15 Claims, No Drawings

5-[(HETEROARYL)ALKYL]-3-OXO-PYRIDO[1,2-A]BENZIMIDAZOLE-4-CARBOXAMIDE DERIVATIVES USEFUL IN TREATING CENTRAL NERVOUS SYSTEM DISORDERS

BACKGROUND OF THE INVENTION

The gamma-aminobutyric acid-A receptor (GABA-A receptor) is the most abundant inhibitory receptor in mammalian brain. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Smith and Olsen, *Trends Pharm. Sci.*, 1995, 16, 162; Stephenson, *Biochem. J.*, 1995, 310, 1). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. *J. Med. Chem.* 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. *Arzneim.-Forsch/Drug Res.*1992, 42 (2a), 211; Haefely, W. et al., *Advances in Drug Research*, Academic Press, vol. 14, 1985, pp. 165–322; Skolnick, P. et al., *GABA and Benzodiazepine Receptors*, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are useful for the treatment of benzodiazepine drug overdose and inverse agonists are useful in managing alcoholism.

The present invention is concerned with novel compositions of matter and their use. Compounds having some structural similarity to those of the present invention are described in Rida, S. M. et al. *J. Het. Chem.* 1988, 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t); Ohta, S. et al. *Heterocycles* 1991, 32, 1923; Ohta, S. et al. *Chem. Pharm. Bull.* 1991, 39, 2787. In addition, structurally similar compounds are disclosed in U.S. application Ser. No. 08/943,578, Oct. 3, 1997, assigned to the assignee of the present invention.

SUMMARY OF THE INVENTION

The present invention is directed to compounds of the following formula 1:

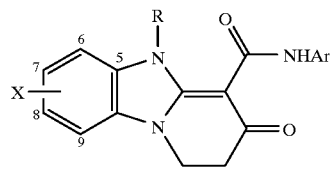

wherein R, Ar, and X are as defined hereinafter. The compounds of formula 1 are useful in treating central nervous system disorders. The compounds are ligands for the BZD binding site on GABA-A receptors, and are thus useful as muscle relaxants, hypnotics/sedatives including sleep-aids, anxiolytics, anticonvulsants/antiepileptics, anti-inebriants, and antidotes for drug overdose (particularly benzodiazepine overdose).

The present invention also comprises pharmaceutical compositions containing one or more of the compounds of formula 1 and methods for the treatment of disorders to the central nervous system including convulsions such as epileptic seizures, anxiety, muscular spasms, sleep disorders, and benzodiazepine overdoses employing a compound of formula 1.

DETAILED DESCRIPTION OF THE INVENTION

More specifically, the invention is directed to compounds of the following formula 1:

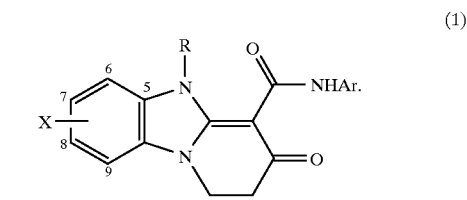

wherein X is independently selected from any of hydrogen, $C_1$–$C_8$ alkyl, halogen, perfluoro($C_1$–$C_8$ alkyl), hydroxy, $C_1$–$C_8$ alkoxy, di($C_1$–$C_8$ alkyl) amino, $C_1$–$C_8$ alkoxycarbonyl or $C_1$–$C_8$ alkylthio. There may be up to four independent X substituents on the phenyl. More preferably, X is selected from any of $C_1$–$C_8$ alkoxy, hydrogen, halogen or $C_1$–$C_8$ alkyl. Preferably, there is only one X substituent other than hydrogen. Most preferably, such other X substituent is fluoro.

R is selected from any of $(CH_2)_n$-heterocycle where n=1–4 and the heterocycle is selected from any of morpholine, pyridine, pyridine-N-oxide, thiazole, thiophene, furan, indole, benzothiophene, pyridazine, pyrimidine, indoline, quinoline, indazole, imidazole, benzofuran, triazine, pyrazine, isoquinoline, isoxazole, thiadiazole, benzothiazole, triazole, benzotriazole, or substituted piperazine where the substituent is hydrogen or lower alkyl; a substituted heterocycle where there are one or more substituents which are independently selected from any of halogen, perfluoro(lower)alkyl, nitro, lower alkylthio, lower alkoxy, lower alkyl, di(lower alkyl)amino, carboxy, or lower alkoxycarbonyl. More preferably, R is selected from any of (2-furfuryl)methyl; (4-imidazo)methyl; (3-pyridyl-N-oxide)methyl; (4-pyridyl-N-oxide)methyl; 2-(2-pyridyl)ethyl; (4-pyridyl)methyl; (3-pyridyl)methyl; 2-(2-thienyl)ethyl; (3-thienyl)methyl; 2-(3-thienyl)ethyl; (2-thienyl)methyl; (2-pyridyl)methyl; 2-(3-thienyl)ethyl; and (3

-furfuryl)methyl. Most preferably, R is selected from any of 2-(3-thienyl)ethyl; 3-(2-thienyl)ethyl; 2-and 3-(thienyl) methyl and 4-(imidazo)methyl.

Ar is selected from any of phenyl and substituted phenyl, where the phenyl substituents are $C_1$–$C_8$ alkyl, halogen, perfluoro(lower alkyl), hydroxy, lower alkoxy, di(lower alkyl) amino, lower alkoxycarbonyl or lower alkylthio; a heterocycle where heterocycle is selected from any of pyridine, pyridine-N-oxide, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole; a substituted heterocycle where there are one or more substituents which are independently selected from any of halogen, perfluoro (lower)alkyl, nitro, lower alkylthio, lower alkoxy, lower alkyl, di(lower alkyl)amino, carboxy, lower alkoxycarbonyl. More preferably, Ar is selected from any of 2-fluorophenyl, 2,6-difluorophenyl, 4-methoxyphenyl, and 2-fluoro-4-methoxyphenyl.

As used herein unless otherwise noted alkyl and alkoxy whether used alone or as part of a substituent group, include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. Unless otherwise noted, "lower" when used with alkyl and alkoxy means a carbon chain composition of 1–8 carbon atoms. Of course, if the alkyl or alkoxy substituent is branched there must be at least 3 carbons.

The term "aryl" as used herein alone or in combination with other terms indicates aromatic hydrocarbon groups such as phenyl or naphthyl. The term "aralkyl" means a radical containing a lower alkyl group substituted with an aryl radical. With reference to substituents, the term independently means that when more than one of such substituent is possible, such substituents may be the same or different from each other.

Examples of particularly preferred compounds of formula 1 include:

7-Fluoro-1,2-dihydro-5-[2-(3-thienyl)ethyl]-3-oxo-N-(2-fluorophenyl)pyrido-[1,2-a]benzimidazole-4-carboxamide, 7-Fluoro-1,2-dihydro-5-[2-(2-thienyl)ethyl]-3-oxo-N-(2-fluorophenyl)pyrido-[1,2-a]benzimidazole-4-carboxamide, 7-Fluoro-1,2-dihydro-5-[(2-thienyl)methyl]-3-oxo-N-(2-fluorophenyl)pyrido-[1,2-a]benzimidazole-4-carboxamide, 7-Fluoro-1,2-dihydro-5-[(3-thienyl)methyl]-3-oxo-N-(2-fluorophenyl)pyrido-[1,2-a]benzimidazole-4-carboxamide, and 7-Fluoro-1,2-dihydro-5-[(4-imidazo)methyl]-3-oxo-N-(2-fluorophenyl)pyrido-[1,2-a]benzimidazole-4-carboxamide.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can are made by reacting the free base of compounds of formula 1 with the acid and isolating the salt.

Hydrates and other solvates of the compound of formula 1 are also included within the scope of this invention and included within the definition of formula 1.

The compounds of formula 1 are prepared as outlined in the following Scheme 1.

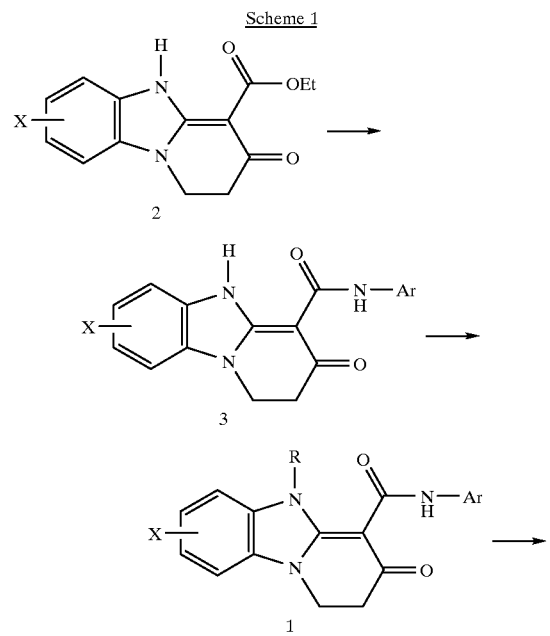

More specifically, the pyridobenzimidazole ester derivative 2 is manufactured according to the following Scheme 2.

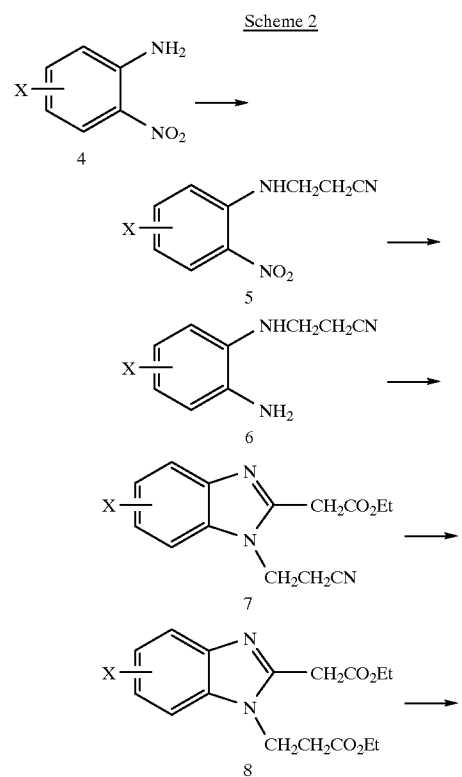

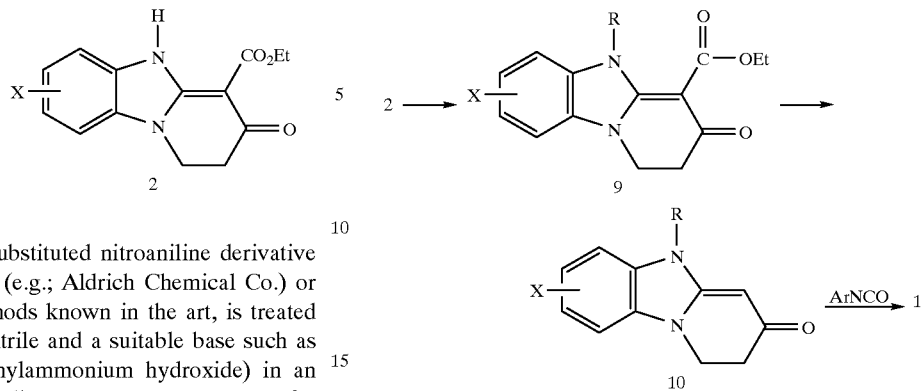

More specifically, the substituted nitroaniline derivative 4, commercially available (e.g.; Aldrich Chemical Co.) or prepared by standard methods known in the art, is treated with a mixture of acrylonitrile and a suitable base such as Triton B (N-benzyltrimethylammonium hydroxide) in an appropriate solvent such as dioxane at room temperature for 1–4 days to give the desired nitrile derivative 5. The nitro group of the nitrile derivative 5 is reduced to give the amino derivative 6 by treatment of said derivative with a suitable reduction catalyst such as Pd/C in an appropriate solvent such as ethyl acetate under a hydrogen atmosphere of about 50–60 psig for about 3–12 h. The benzimidazole derivative 7 is prepared by heating the amino derivative 6 with ethyl ethoxycarbonylacetimidate.HCl in a suitable solvent such as EtOH for about 4–24 h. Treatment of benzimidazole derivative 7 with an anhydrous acid such as HCl(g) in an appropriate solvent such as EtOH at reflux for about 4–24 h gives the diester derivative 8. The diester is treated with a suitable base such as sodium ethoxide in an appropriate solvent such as EtOH for about 12–24 h at room temperature followed by treatment with ethanolic HCl to give pyridobenzimidazole 2.

The pyridobenzimidazole ester derivative 2 is then heated to reflux with an appropriate substituted amine derivative in a suitable solvent such as xylene or dimethyl formamide for about 1–24 h to give the pyrido[1,2-a]benzimidazole amide derivative 3.

The pyridobenzimidazole derivative 3 is selectively alkylated at the N5 position using the method of Mitsunobu (see Hughes, D. Organic Reactions, 42, 355–656) or the recently reported modified procedures (see Tsunoda Tetrahedron Letters 1993, 34 1639–1642 and Tsunoda Chemistry Letters 1994, 539–542). Treatment of pyridobenzimidazole derivative 3 with an appropriate heterocyclic alkanol such as 2-(3-thienyl)ethanol and 2-furanylmethanol and 1–5 equivalents of a suitable activating agent such as diethylazodicarboxylate (DEAD), azodicarbonyldipiperidine (ADDP), or 1,1-azobis(N,N-dimethylformamide) (TMAD) and an appropriate trisubstituted phosphine such as triphenylphosphine or tributylphosphine in an appropriate solvent such as benzene, THF, or DMF at about 0° C. to room temperature for about 1–24 hr provided the desired N5-(heteroaryl)alkyl pyridobenzimidazole derivatives 1.

Alternatively, compounds of the invention could be prepared according to Scheme 3 by taking ester 2 and deprotonating N5 with a base such as NaH or $K_2CO_3$, and then reacting the subsequent anion with an alkyl halide such as 2-picolyl halide in a suitable solvent such as DMF or DMSO to give esters of type 9. These are then treated with a base such as NaOH (3N in ethanol) with heating to give enaminones of type 10. Reaction of compounds of type 10 with isocyanates typically at room temperature in a solvent such as 1,2-dichloroethane affords target compounds of type 1.

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Table 1.

Benzodiazepine Receptor Binding Assay

Selected compounds, which were prepared according to the experimental details given in the following examples, were tested for binding to the benzodiazepine site of the GABA-A receptor (Williams, M. et al., J. Pharm. Exper. Therap. 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 25° C., after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Table 1. An $IC_{50}$ value of over 10,000 for a particular compound would indicate that the compound was not active in this screen. This is a general screen and compounds active here are have potential utility for the treatment of one or more disorders of the central nervous system.

Assay to Determine the Suppression of Metrazol-Induced Convulsions in Adult Male Mice Compounds of the invention were tested for their ability to reduce metrazol-induced convulsions in mice (Swinyard, E. A. J. Am. Pharm Assoc. 1949, 38, 201). Male $CD_1$ mice, were fasted at least 16 hours, were divided into equal groups and test compounds or vehicle were administered parenterally. Water was not withheld except during the period of observations. At the time of suspected peak activity, antipentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 mL/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Table 1. An $ED_{50}$ value of greater than 30 indicates that an active dose for the compound being tested had not been determined. Compounds active in this screen are considered active anticonvulsion/antiepileptic agents.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hrs and were deprived of food for 24 hrs prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase (p<0.05, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1 to 5. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

TABLE 1

Biological activity of the compounds of formula I:

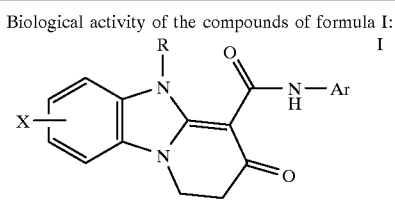

| CP# | Ar | R | X | IC50 nM | Mouse Metrazol (ip, mg/kg) (ip, mg/kg) ED50 | Rat Conflict MED |
|---|---|---|---|---|---|---|
| 11 | 2-fluorophenyl | (2-furfuryl)methyl | 7-fluoro | 0.59 | <10 | >10 |
| 12 | 2-fluorophenyl | (4-imidazo)methyl | 7-fluoro | 0.29 | 30 | >10 |
| 13 | 2-fluorophenyl | (3-pyridyl-N-oxide)methyl | 7-fluoro | 5.19 | 3 | >10 |
| 14 | 2-fluorophenyl | (4-pyridyl-N-oxide)methyl | 7-fluoro | 13.4 | 10 | >10 |
| 15 | 2-fluorophenyl | 2-(2-pyridyl)ethyl | 7-fluoro | 0.89 | 0.3 | 10 |
| 16 | 2-fluorophenyl | (4-pyridyl)methyl | 7-fluoro | 3.01 | 3 | >10 |
| 17 | 2-fluorophenyl | (3-pyridyl)methyl | 7-fluoro | 1.27 | 1 | >10 |
| 18 | 2,6-difluorophenyl | 2-(2-thienyl)ethyl | 7-fluoro | 0.61 | 10 | >10 |
| 19 | 2-fluorophenyl | (3-thienyl)methyl | 7-fluoro | 0.71 | 0.7 | <10 |
| 20 | 2-fluorophenyl | 2-(3-thienyl)ethyl | 7-fluoro | 0.096 | 0.1 | <10 |
| 21 | 2-fluorophenyl | (2-thienyl)methyl | 7-fluoro | 0.30 | <1 | <10 |
| 22 | 2-fluorophenyl | (2-pyridyl)methyl | 7-fluoro | 2.79 | <1 | <10 |
| 23 | 2,6-difluorophenyl | (3-thienyl)methyl | 7-fluoro | 4.24 | >10 | >10 |
| 24 | 2,6-difluorophenyl | (2-pyridyl)methyl | 7-fluoro | 24.4 | 3 | 10 |
| 25 | 2,6-difluorophenyl | 2-(3-thienyl)ethyl | 7-fluoro | 0.22 | 3 | <10 |
| 26 | 2,6-difluorophenyl | (2-thienyl)methyl | 7-fluoro | 2.98 | <10 | >10 |
| 27 | 2,6-difluorophenyl | (2-furfuryl)methyl | 7-fluoro | 1.26 | 1 | >10 |
| 28 | 2-fluorophenyl | (2-pyridyl)methyl | H | 3.77 | 0.5 | <10 |
| 29 | 2,6-difluorophenyl | (2-pyridyl)methyl | H | 23.9 | 3 | >10 |
| 30 | 2-fluorophenyl | (3-pyridyl)methyl | H | 4.54 | 10 | 10 |

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use in treating disorders of the central nervous system in mammals, the compounds of this invention may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to 25 mg/kg per day. In therapeutic use as an agent for treating benzodiazepine overdoses, the compounds of the invention may be administered in an amount from about 0.2 to 25 mg/kg per day. In therapeutic use as a sedative/hypnotic, a therapeutically effective amount is from about 0.2 to 25 mg/kg per day. As a muscle relaxant about 0.2 to 25 mg/kg per day of the compounds of this invention may be used. Determination of optimum dosages for a particular situation is within the skill of the art.

EXAMPLES

The following examples describe the invention in greater detail and are intended to illustrate the invention, but not to limit it.

Melting point determinations were carried out on a Thomas Hoover or Mel-Temp melting point apparatus and are uncorrected. Each compound has at least two analytical results (elemental analysis, mp) given here. Nuclear magnetic resonance (NMR) spectra for hydrogen atoms were measured in the indicated solvent with tetramethylsilane (TMS) as the internal standard on a Bruker AM-360 (360 MHz) or AT-300 (300 MHz) spectrometer. The values are expressed in parts per million downfield from TMS. Elemental analyses were measured by Robertson Microlit (Madison, N.J.) and are expressed in percentage by weight of each element per total molecular weight. The mass spectra (MS) were determined on a Finnigan 3300 spectrometer (methane), using desorption chemical ionization techniques. All preparative column chromatography were run using a Waters Prep 500A HPLC (silica gel) employing the appropriate commercially available solvent. Unless otherwise noted, the materials used in the examples were obtained from readily available commercial suppliers or synthesized by standard methods known to anyone skilled in the art of chemical synthesis. The substituent groups, which vary between examples are hydrogen unless otherwise noted.

Example 1 (20)

7-Fluoro-1,2-dihydro-5-[2-(3-thienyl)ethyl]3-oxo-N-(2-fluorophenyl)pyrido[1,2-a]benzimidazole-4-carboxamide Compound 3 (X=7-F, Ar=2-FPh; 1.0 g, 2.92 mmol) was dissolved in 75 mL dry THF with stirring under argon. To this solution was added 2-(3-thienyl)ethanol (1.12 g, 8.76 mmol) and triphenylphosphine (2.29 g, 8.76 mmol). The solution was stirred for 10 min, and then cooled to 0° C. with an ice water bath. Diethylazodicarboxylate (1.52 g, 8.76 mmol) was added dropwise. The ice bath was removed and the solution was stirred at room temperature overnight. The reaction mixture was concentrated in vacuo to yield a dark yellow oil. The oil was purified by MPLC chromatography (silica gel; 1.5:98.5 methanol/methylene chloride). The resultant solid was recrystallized from isopropanol to yield 20 (0.69 g, 52.4%) as a white crystalline solid; mp 222.8–224.4° C. H-1 NMR (Me$_2$SO-d$_6$) δ 12.38–12.20 (s, 1H), 8.54–8.45 (t, 1H), 7.90–7.75 (m, 1H), 7.73–7.61 (m, 1H), 7.4–7.32 (m, 1H), 7.3–6.92 (m, 5-H), 6.9–6.81 (d, 1H), 4.75–4.61 (m, 2H), 4.38–4.30 (m, 2H), 3.05–2.92 (m, 2H), 2.71–2.59 (m, 2H). Cl-MS m/e 452 (MH$^+$).

In like manner were prepared the following compounds of the present invention were made:

| CP# | mp (° C.) | % Yield |
|---|---|---|
| 11 | 202–209 | 31.6 |
| 12 | 210–230 (dec) | 34 |
| 13 | 231.3–232.3 | 34 |
| 19 | 173.7–174.9 | 62 |
| 21 | 188.6–190.2 | 63 |
| 22 | 223–231 (dec) | 80 |

Example 2 (#17)

7-Fluoro-1,2-dihydro-5-(3-pyridylmethyl)-3-oxo-N-(2-fluorophenyl)pyrido[1,2-a]benzimidazole-4-carboxamide Compound 3 (X=7-F, Ar=2-FPh; 1.0 g, 2.92 mmole) was dissolved in 75 mL dry THF with stirring under argon. To the solution was added 3-pyridylcarbinol (2, 0.647 g, 5.84 mmole) and tri-n-butylphosphine, (1.18 g, 5.84 mmole). The solution was stirred for ten minutes, then cooled to 0° C. with an ice bath. 1,1-Azobis(N,N-dimethylformamide) (1.00 g, 5.84 mmole) was added in one portion. The ice bath was removed and the solution was stirred overnight at room temperature. The solvent was removed by rotary evaporation in vacuo to yield a yellow solid, which was chromatographed by MPLC on silica gel 60 (200–400 mesh) with 3% methanol/96.75% methylene chloride/0.25% triethylamine to yield a white solid. This material was recrystallized from isopropanol to yield compound 17 (0.630 g, 51%) as a white crystalline solid, mp 158.6–159.6° C. H-1 NMR (Me$_2$SO-d$_6$) δ 12.21–12.15 (s, 1H, CONH), 8.5–8.4 (m, 3H), 7.80–7.71 (m, 1H), 7.69–7.62 (m, 1H, 4-pyridyl), 7.51–7.47 (m, 1H), 7.3–6.92 (m, 5H), 5.88–5.71 (s, 2H), 5.45–5.41 (s, 2H), 4.38–4.30 (m, 2H), 3.42–3.39 (s, 1H), 2.78–2.69 (m, 2H). Cl-MS: m/e 424 (MH$^+$).

In like manner, the following compounds of the present invention were prepared:

| CP# | mp | % Yield |
|---|---|---|
| 14 | 206.9–208.7° C. | 43 |
| 15 | 160.9–161.9° C. | 37 |
| 16 | 213.1–214.7 | 63 |

Example 3 (#25)

7-Fluoro-1,2-dihydro-5-[2-(3-thienyl)ethyl]-3-oxo-N-(2-fluorophenyl)pyrido[1,2-a]benzimidazole-4-carboxamide Compound 3 (X=F, Ar=2,6-F2Ph; 1.0 g, 2.78 mmol) was dissolved in 70 mL dry benzene with stirring under argon. To the solution was added 2-(3-thienyl)ethanol (0.5343 g, 4.17 mmol) and tri-n-butylphosphine (0.843 g, 4.168 mmol). The solution was stirred for 10 min, then cooled to 0° C. with an ice water bath. Azodicarbonyldipiperidine (1.051 g, 4.168 mmole) was added in one portion. The ice bath was removed and the solution stirred at room temperature overnight. The solvent was removed by rotary evaporation in vacuo to yield a dark yellow solid. The solid was recrystallized from isopropanol to yield compound 25 (0.4157 g, 21%) as a white crystalline solid, mp 166.5–167.2° C. H-1 NMR (Me$_2$SO-d$_6$) δ 11.52–11.42 (s, 1H, CONH), 8.54–8.45 (t, 1H), 7.90–7.75 (m, 1H), 7.79–7.61 (m, 1H), 7.4–7.32 (m, 1H), 7.3–6.92 (m, 4-H), 6.9–6.85 (d, 1H), 4.75–4.61 (m, 2H), 4.38–4.30 (m, 2H), 3.05–2.92 (m, 2H), 2.71–2.59 (m, 2H). Cl-MS: m/e 470 (MH$^+$).

In like manner, the following compounds of the present invention were prepared:

| CP# | mp | % Yield |
|---|---|---|
| 18 | 180.5–182.2 | 27 |
| 23 | 215–223 (dec) | 68 |
| 24 | 225–235 (dec) | 53 |
| 26 | 222.7–229.3 | 57 |
| 27 | 210 (dec) | 36 |

Example 4 (28)

1,2-Dihydro-5-(2-pyridylmethyl)-3-oxo-N-(2-fluorophenyl)pyrido[1,2-a]-benzimidazole-4-carboxamide Sodium hydride (60% in mineral oil; 9.80 g, 245 mmol) was rinsed with pentane (2×100 mL) and covered with anhydrous DMF (175 mL). This suspension was cooled in a ice water bath (10° C.). Then the pyridobenzimidazole ester (2, X=H, 10.32 g, 40.0 mmol) was added in one portion. The resultant insoluble sodium salt of the PBI ester was covered with additional DMF (40 mL) and subsequently treated with 2-picolyl chloride hydrochloride (32.81 g, 200 mmol). The reaction mixture was diluted with H$_2$O (200 mL) and extracted with CHCl$_3$ (3×200 mL). The CHCl$_3$ solution was washed with aqueous 1N NaOH (3×150 mL), H$_2$O (4×250 mL), dried (Na$_2$SO$_4$) and concentrated to provide 20.87 g of a crude dark reddish solid (9, X=H, R=2-pyridylmethyl). This crude product was carried on to decarbethoxylation without further purification. MS (Cl—CH$_4$) m/e 350 (MH$^+$). A solution of the sample of 9 prepared above (20.77 g), and aqueous 3N NaOH (200 mL) in ethanol (300 mL) was heated to reflux for 7 hr and then kept at room temperature for 3 d. The ethanol was removed in vacuo providing a brown residue which was diluted with H$_2$O (100 mL) and extracted with CHCl$_3$ (3×150 mL). The combined CHCl$_3$ solution was washed with H$_2$O (150 mL), brine (2×150 mL), dried (Na$_2$SO$_4$), and concentrated to provide a brown moist solid (12.7 g). This solid was covered with Et$_2$O and filtered to furnish 5.67 g of product enaminone 10 (X=H, R=2-pyridylmethyl) as a brown powder. Cl-MS (CH$_4$) m/e 278 (MH$^+$). A solution of enaminone 10 prepared above (1.39 g, 5.00 mmol) and 2-(fluoro)phenylisocyanate (0.70 mL, 6.23 mmol) in dichloroethane (50 mL) was stirred at room temperature for 40 hr. The solvent was removed in vacuo and the crude product was chromatographed on silica gel (2:98 MeOH/CHCl$_3$) to provide 1.84 g of a light brown solid. This free base was dissolved in 75 mL of 2:1 CHCl$_3$/MeOH mixture, filtered, and acidified with concentrated HCl in iPrOH until the pH was 3. Recrystallization of the HCl salt of 28 from MeOH/Et$_2$O provided 1.15 g (51%) of a white amorphous solid, mp 213–216° C. (dec.) H-1 NMR (300 MHz, DMSO-d$_6$) δ 12.2 (s, 1H, amide NH), 8.6 (d, 1H), 8.4 (t, 1H), 7.9 (t, 1H), 7.75 (d, 1H), 7.5 (m, 4H), 7.35 (m, 1H), 7.25 (m, 1H), 7.10 (m, 1H), 5.9 (s, 2H), 4.4 (t, 2H), 2.75 (s, 2H).

In like manner the following compounds of the present invention were prepared:

| CP# | mp | % Yield |
|---|---|---|
| 29 | 187–193 | 62 |
| 30 | 197–204 | 38 |

TABLE 2

Physical Properties of N-5 (Heteroaryl)alkyl PBI Derivatives.

| CP# | Calc. C | Calc. H | Calc. N | Found C | Found H | Found N | Empirical Formula |
|---|---|---|---|---|---|---|---|
| 11 | 65.55 | 4.07 | 9.97 | 65.20 | 4.00 | 9.83 | C$_{23}$H$_{17}$F$_2$N$_4$O$_3$ |
| 12 | 57.71 | 3.96 | 14.30 | 57.32 | 3.95 | 15.29 | C$_{23}$H$_{17}$F$_2$N$_5$O$_2$ |
| 13 | 64.28 | 4.05 | 12.49 | 64.05 | 3.92 | 12.32 | C$_{24}$H$_{18}$F$_2$N$_4$O$_3$ |
| 14 | 60.63 | 4.45 | 11.78 | 60.73 | 4.45 | 11.78 | C$_{24}$H$_{18}$F$_2$N$_4$O$_3$ |
| 15 | 66.50 | 4.60 | 12.40 | 66.31 | 4.27 | 12.24 | C$_{25}$H$_{20}$F$_2$N$_4$O$_2$·0.3H$_2$O |
| 16 | 66.66 | 4.20 | 12.96 | 66.55 | 4.02 | 12.95 | C$_{24}$H$_{18}$F$_2$N$_4$O$_2$ |
| 17 | 66.66 | 4.20 | 12.96 | 66.51 | 4.14 | 12.79 | C$_{24}$H$_{18}$F$_2$N$_4$O$_2$ |

TABLE 2-continued

Physical Properties of N-5 (Heteroaryl)alkyl PBI Derivatives.

| CP# | Calc. C | Calc. H | Calc. N | Found C | Found H | Found N | Empirical Formula |
|---|---|---|---|---|---|---|---|
| 18 | 61.17 | 3.89 | 8.92 | 60.97 | 3.76 | 8.85 | $C_{24}H_{18}F_3N_4O_2S.0.1H_2O$ |
| 19 | 63.15 | 3.92 | 9.61 | 62.94 | 3.87 | 9.35 | $C_{23}H_{17}F_2N_4O_2S$ |
| 20 | 63.85 | 4.24 | 9.31 | 63.60 | 4.21 | 9.18 | $C_{24}H_{19}F_2N_4O_2S$ |
| 21 | 62.63 | 3.98 | 9.53 | 62.71 | 3.92 | 9.41 | $C_{23}H_{17}F_2N_4O_2.H_2O$ |
| 22 | 65.84 | 4.28 | 12.8 | 65.81 | 4.15 | 12.77 | $C_{24}H_{18}F_2N_4O_2.0.3H_2O$ |
| 23 | 60.65 | 3.54 | 9.23 | 60.30 | 3.33 | 9.08 | $C_{23}H_{16}F_3N_4O_2S$ |
| 24 | 64.00 | 3.80 | 12.44 | 63.80 | 3.66 | 12.33 | $C_{24}H_{17}F_3N_4O_2$ |
| 25 | 61.40 | 3.86 | 8.95 | 61.42 | 3.72 | 8.86 | $C_{24}H_{18}F_3N_4O_2S$ |
| 26 | 60.65 | 3.54 | 9.23 | 60.42 | 3.45 | 9.11 | $C_{23}H_{16}F_3N_4O_2S$ |
| 27 | 62.87 | 3.67 | 9.56 | 62.67 | 3.55 | 9.54 | $C_{23}H_{16}F_3N_4O_2$ |
| 28 | 63.93 | 4.47 | 12.43 | 63.81 | 4.48 | 12.36 | $C_{24}H_{19}FN_4O_2.HCl$ |
| 29 | 54.09 | 3.59 | 10.51 | 54.05 | 3.30 | 10.47 | $C_{24}H_{18}F_2N_4O_2.HClO_4$ |
| 30 | 61.47 | 4.73 | 11.95 | 61.81 | 4.81 | 11.78 | $C_{24}H_{19}FN_4O_2.HCl.H_2O$ |

What is claimed is:

1. A compound of the formula 1:

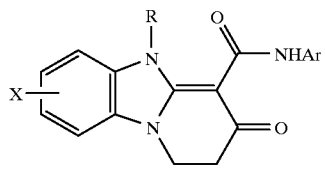

(1)

wherein X is independently selected from any of hydrogen, $C_1$–$C_8$ alkyl, halogen, perfluoro($C_1$–$C_8$ alkyl), hydroxy, $C_1$–$C_8$ alkoxy, di($C_1$–$C_8$ alkyl)amino, $C_1$–$C_8$ alkoxycarbonyl or $C_1$–$C_8$ alkylthio;

wherein R is selected from any of $(CH_2)_n$-heterocycle where n=1–4 and wherein the heterocycle is an optionally subsituted heterocycle selected from any of pyridine, pyridine-N-oxide, thiazole, thiophene, furan, indole, benzothiophene, indoline, quinoline, indazole, imidazole, benzofuran, isoquinoline, isoxazole, thiadiazole, benzothiazole, triazole or benzotriazole, wherein the substituents are independently selected from one or more of halogen, perfluoro(lower)aklyl, nitro, lower akylthio, lower alkoxy, lower alkyl, di(lower alkyl)amino, carboxy or lower alkoxycarbonyl;

wherein Ar is selected from any of phenyl and substituted phenyl, wherein the phenyl substituents are $C_1$–$C_8$ alkyl, halogen, perfluoro(lower)aklyl, hydroxy, lower alkoxy, di(lower alkyl)amino, lower alkoxycarbonyl or lower alkylthio; or an optionally subsituted heterocycle selected from any of pyridine, pyridine-N-oxide, thiazole, thiophene, furan, indole, benzothiophene, indoline, quinoline, indazole, imidazole, benzofuran, isoquinoline, isoxazole, thiadiazole, benzothiazole, triazole or benzotriazole wherein the substituents are independently selected from one or more of halogen, perfluoro(lower)aklyl, nitro, lower akylthio, lower alkoxy, lower alkyl, di(lower alkyl)amino, carboxy or lower alkoxycarbonyl;

or a pharmaceutically acceptable salt, solvate, hydrate, tautomer or rotomer thereof.

2. The compound of claim 1, wherein there is only one X substituent other than hydrogen.

3. The compound of claim 2, wherein the X substituent other than hydrogen is fluoro.

4. The compound of claim 1, wherein R is selected from any of (2-furfuryl)methyl; (4-imidazolyl)methyl; (3-pyridyl-N-oxide)methyl; (4-pyridyl-N-oxide)methyl; 2-(2-pyridyl)ethyl; (4-pyridyl)methyl; (3-pyridyl)methyl; 2-(2-thienyl)ethyl; (3-thienyl)methyl; 2-(3-thienyl)ethyl; (2-thienyl)methyl; (2-pyridyl)methyl; 2-(3-thienyl)ethyl; and (3-furfuryl)methyl.

5. The compound of claim 4, wherein R is 4-(imidazolyl)methyl.

6. The compound of claim 1, wherein Ar is selected from either of 2-fluorophenyl, 2,6-difluorophenyl.

7. The compound of claim 1, selected from any of

7-Fluoro-1,2-dihydro-5-[2-(3-thienyl)ethyl]-3-oxo-N-(2-fluorophenyl)pyrido-[1,2-a]benzimidazole-4-carboxamide, 7-Fluoro-1,2-dihydro-5-[2-(2-thienyl)ethyl]-3-oxo-N-(2-fluorophenyl)pyrido-[1,2-a]benzimidazole-4-carboxamide, 7-Fluoro-1,2-dihydro-5-[(2-thienyl)methyl]-3-oxo-N-(2-fluorophenyl)pyrido-[1,2-a]benzimidazole-4-carboxamide, 7-Fluoro-1,2-dihydro-5-[(3-thienyl)methyl]-3-oxo-N-(2-fluorophenyl)pyrido-[1,2-a]benzimidazole-4-carboxamide, and 7-Fluoro-1,2-dihydro-5-[(4-imidazo)methyl]-3-oxo-N-(2-fluorophenyl)pyrido-[1,2-a]benzimidazole-4-carboxamide.

8. A pharmaceutical composition comprising the compound of formula 1 of claim 1, in an amount effective for treating disorders of the central nervous system and a pharmaceutically acceptable carrier or diluent.

9. A method of treating a disorder of the central nervous system selected from the group consisting of anxiety, epileptic seizures, convulsions, sleeplessness and muscle spasms in a mammal in need thereof comprising administering to the mammal a compound of formula 1 of claim 1 in an amount effective for treating such disorder.

10. The method of claim 9, wherein the effective amount is of from about 0.2 to 25 mg/kg per day.

11. The method of claim 9, wherein the disorder is anxiety.

12. The method of claim 9 wherein the disorder is convulsions.

13. The method of claim 9 wherein the disorder is sleeplessness.

14. The method of claim 9 wherein the disorder is muscle spasm.

15. A method of treating benzodiazepine drug overdose in a mammal in need thereof comprising administering to the mammal a compound of formula 1 of claim 1 in an amount effective for treating such overdose.

* * * * *